United States Patent
Govari et al.

(10) Patent No.: US 12,383,235 B2
(45) Date of Patent: Aug. 12, 2025

(54) ULTRASOUND IMAGING OF CARDIAC ANATOMY USING DOPPLER ANALYSIS

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/495,282

(22) Filed: Oct. 26, 2023

(65) Prior Publication Data
US 2024/0050073 A1    Feb. 15, 2024

Related U.S. Application Data

(62) Division of application No. 17/483,097, filed on Sep. 23, 2021, now abandoned.

(51) Int. Cl.
    A61B 8/00    (2006.01)
    A61B 8/08    (2006.01)
    A61B 8/12    (2006.01)

(52) U.S. Cl.
    CPC .......... *A61B 8/5207* (2013.01); *A61B 8/0883* (2013.01); *A61B 8/12* (2013.01);
    (Continued)

(58) Field of Classification Search
    CPC ....... A61B 8/5207; A61B 8/0883; A61B 8/12; A61B 8/4488; A61B 8/4494; A61B 8/461;
    (Continued)

(56) References Cited

U.S. PATENT DOCUMENTS

| 5,622,174 A | 4/1997 | Yamazaki |
| 5,882,302 A * | 3/1999 | Driscoll, Jr. ............. A61B 8/06 600/371 |

(Continued)

FOREIGN PATENT DOCUMENTS

| EP | 3682810 A1 | 7/2020 |
| WO | WO9605768 | 2/1996 |

OTHER PUBLICATIONS

Sutherland, G.R. "Colour DMI: potential applications in acquired and congenital heart disease," Acta Paediatrica, vol. 84, Issue 410, Aug. 1995, pp. 40-48 (Abstract).
(Continued)

*Primary Examiner* — Peter Luong
(74) *Attorney, Agent, or Firm* — Smith, Gambrell & Russell LLP

(57) ABSTRACT

A method includes emitting an ultrasound beam from an array of ultrasound transducers in a catheter placed in a blood pool in an organ. Echo signals reflected in response to the ultrasound beam are received in the array. Distinction is made in the echo signals between (i) first spectral signal components having Doppler shifts characteristic of blood and (ii) second spectral signal components having Doppler shifts characteristic of tissue of the organ. The first spectral signal components are suppressed relative to the second spectral signal components in the echo signals. An ultrasound image of at least a portion of the organ is reconstructed from the echo signals having the suppressed first spectral signal components. The reconstructed image is displayed to a user.

10 Claims, 3 Drawing Sheets

(52) U.S. Cl.
CPC .......... *A61B 8/4488* (2013.01); *A61B 8/4494* (2013.01); *A61B 8/461* (2013.01); *A61B 8/488* (2013.01); *A61B 8/5276* (2013.01)

(58) Field of Classification Search
CPC ....... A61B 8/488; A61B 8/5276; A61B 8/065; A61B 8/5223; A61B 8/5269; G01S 15/8925; G01S 15/8981
See application file for complete search history.

(56) References Cited

U.S. PATENT DOCUMENTS

| | | |
|---|---|---|
| 6,332,089 B1 | 12/2001 | Acker et al. |
| 6,553,894 B1 | 4/2003 | Hamon et al. |
| 6,618,612 B1 | 9/2003 | Acker et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0116809 A1 | 6/2004 | Chow et al. |
| 2007/0276243 A1 | 11/2007 | Gerard et al. |
| 2008/0146942 A1 | 6/2008 | Dala-Krishna |
| 2008/0161691 A1* | 7/2008 | Zhang ................ G01S 15/8988 600/453 |
| 2008/0281205 A1 | 11/2008 | Naghavi et al. |
| 2013/0303907 A1* | 11/2013 | Corl ...................... A61B 8/488 600/443 |
| 2016/0235485 A1 | 8/2016 | Belohlavek et al. |
| 2020/0077981 A1 | 3/2020 | Grunwald et al. |
| 2020/0260964 A1 | 8/2020 | Collins et al. |
| 2023/0091996 A1 | 3/2023 | Govari et al. |

OTHER PUBLICATIONS

Extended European Search Report dated Feb. 24, 2023 from corresponding EP application 22197019.7-1126.

* cited by examiner

ULTRASOUND IMAGING OF CARDIAC ANATOMY USING DOPPLER ANALYSIS

CROSS-REFERENCE TO RELATED APPLICATION

This application is a divisional of U.S. patent application Ser. No. 17/483,097 filed Sep. 23, 2021, the contents of which are incorporated by reference as if set forth in its entirety herein.

FIELD OF THE INVENTION

The present invention relates generally to medical imaging, and particularly to Doppler ultrasound imaging using an intra-body medical ultrasound probe.

BACKGROUND OF THE INVENTION

Ultrasound Doppler imaging techniques have been previously proposed in the art. For example, Sutherland describes noninvasive ultrasound Doppler myocardial imaging (DMI) in a paper titled, "Colour DMI: potential applications in acquired and congenital heart disease," ACTA PAEDIATRICA, Volume 84, Issue 410, August 1995, pages 40-48. The paper describes a DMI technique that allows colour Doppler imaging of cardiac structures as opposed to blood pool imaging. This is achieved by changing the velocity, filtering and threshold parameters of the standard colour Doppler algorithms. DMI parameters which can be measured are regional tissue velocity, acceleration and reflected Doppler energy. In addition, concomitant changes in the pulsed Doppler algorithms allow interrogation of instantaneous peak velocities during the cardiac cycle in the myocardial region in which the sample volume is placed.

Although the shape of specific elements of the heart, such as an ostium, may be reconstructed using known anatomical mapping methods, such methods typically rely on moving a catheter to touch points on the element. These approaches are computationally intensive and relatively time consuming. It would be useful to have a faster mapping method, and advantageous to have the method be non-contact.

SUMMARY OF THE INVENTION

An embodiment of the present invention that is described hereinafter provides a method including emitting an ultrasound beam from an array of ultrasound transducers in a catheter placed in a blood pool in an organ. Echo signals reflected in response to the ultrasound beam are received in the array. Distinction is made in the echo signals between (i) first spectral signal components having Doppler shifts characteristic of blood and (ii) second spectral signal components having Doppler shifts characteristic of tissue of the organ. The first spectral signal components are suppressed relative to the second spectral signal components in the echo signals. An ultrasound image of at least a portion of the organ is reconstructed from the echo signals having the suppressed first spectral signal components. The reconstructed image is displayed to a user.

In some embodiments, suppressing the first spectral signal components includes filtering out the first spectral signal components from the echo signals.

In some embodiments, suppressing the first spectral signal components includes attenuating the first spectral signal components in the echo signals by at least a given amount.

In an embodiment, the tissue of the organ is a wall tissue of a cardiac chamber.

In another embodiment, the method further includes focusing the emitted ultrasound beam at a given blood volume and receiving in the array echo signals reflected in response to the focused ultrasound beam. In yet another embodiment, focusing the emitted ultrasound beam includes varying a focal length of the beam to variably collect blood Doppler shifted signals from different multiple blood volumes.

There is further provided, in accordance with another embodiment of the present invention, a system including a catheter including an array of ultrasound transducers and a processor. The array of ultrasound transducers is configured to be placed in a blood pool in an organ, to emit an ultrasound beam and to receive echo signals reflected in response to the ultrasound beam. The processor is configured to (a) distinguish, in the echo signals, between (i) first spectral signal components having Doppler shifts characteristic of blood and (ii) second spectral signal components having Doppler shifts characteristic of tissue of the organ, (b) suppress the first spectral signal components relative to the second spectral signal components in the echo signals, (c) reconstruct an ultrasound image of at least a portion of the organ from the echo signals having the suppressed first spectral signal components, and (d) display the reconstructed image to a user.

There is furthermore provided, in accordance with another embodiment of the present invention, a medical imaging system, including an ultrasound probe and a processor. The ultrasound probe is configured for insertion into an organ of a body, with the ultrasound probe including (i) a two-dimensional (2D) ultrasound transducer array, and (ii) a sensor configured to output signals indicative of a position and orientation of the 2D ultrasound transducer array inside the organ. The processor is configured to (a) using the signals output by the sensor, register multiple ultrasound image sections acquired by the 2D ultrasound transducer array, with one another, (b) produce a union of the multiple registered ultrasound image sections, to form a rendering of at least a portion of the organ, and (c) present the rendering to a user.

The present invention will be more fully understood from the following detailed description of the embodiments thereof, taken together with the drawings in which:

DETAILED DESCRIPTION OF EMBODIMENTS

Overview

Figure 1:
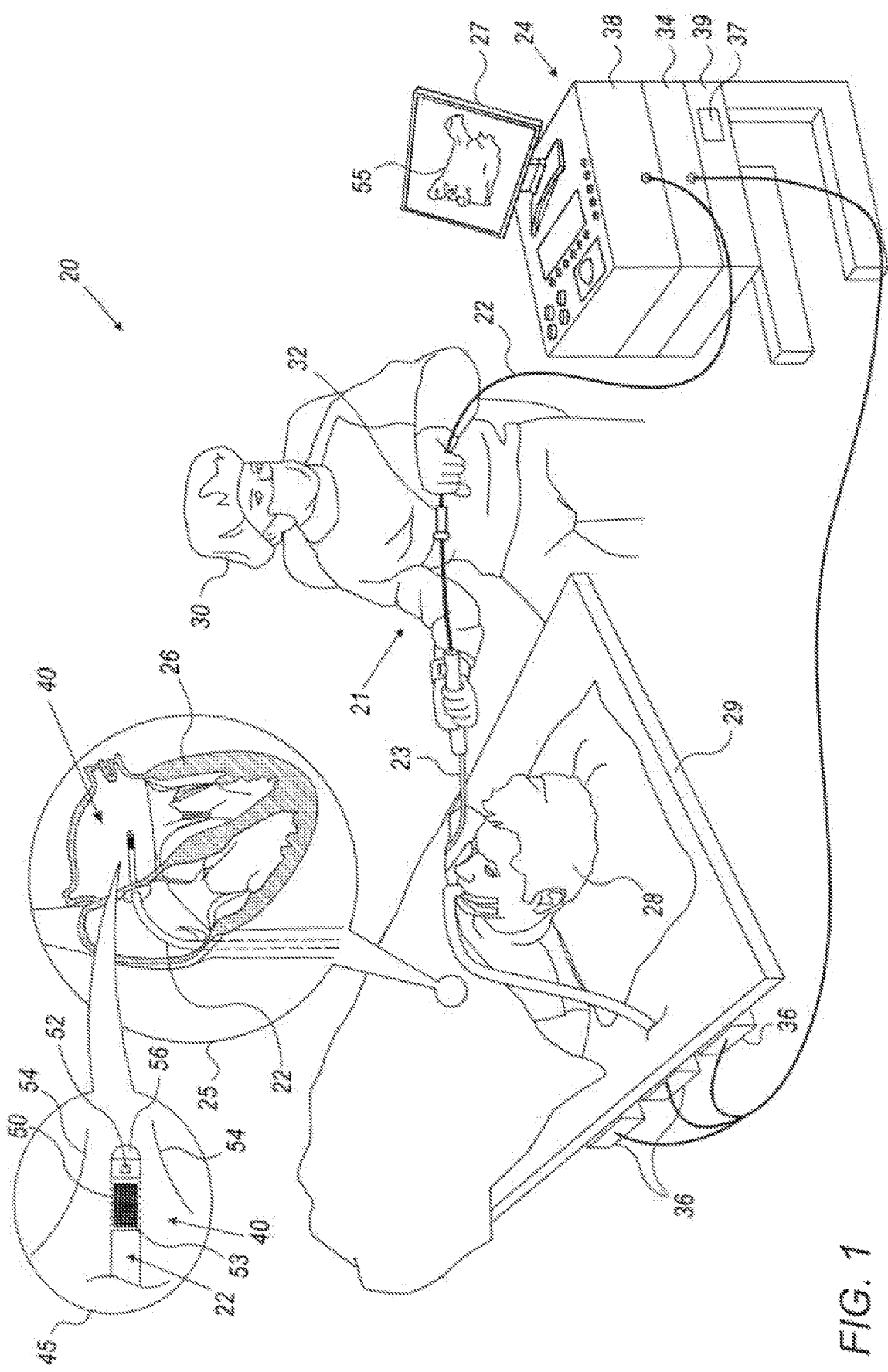
FIG. 1 is a schematic, pictorial illustration of a catheter-based ultrasound imaging system using a catheter with a distal end assembly comprising a 2D ultrasound-array and a location sensor, in accordance with an embodiment of the present invention.

Embodiments of the present invention that are described hereinafter provide methods and systems that use a probe, such as a catheter, having a two-dimensional (2D) array of ultrasound transducers, for producing three-dimensional (3D) or four-dimensional (4D) ultrasound images. In the present context, the term "3D ultrasound image" refers to an ultrasound image that represents a certain volume in three dimensions. The term "4D ultrasound image" refers to a time series of 3D ultrasound images of a certain volume. A 4D image can be regarded as a 3D movie, the fourth dimension being time. Another way of describing a 4D image (or rendering) is as a time-dependent 3D image (or rendering).

The 2D array produces a 3D sector-shaped ultrasound beam occupying a defined solid angle; (such a beam is referred to herein as a "wedge," as opposed to a 1D array "fan"). The 2D array is thus able to image a 2D section of an inner wall of an organ, such as of a cardiac chamber.

In some embodiments, a 4D ultrasound catheter is placed in the blood stream in proximity to an element to be mapped, such as a wall of a cardiac chamber. Subsequently, a processor analyzes reflected signals (e.g., echoes) from the ultrasound wedge beam transmitted by the catheter. Typically, the element of the heart is moving as the heart beats, as is the blood flowing through the heart. Both movements create Doppler shifts in the frequencies of the signals received by the transducers, but the flow of the blood, typically of the order of m/s, is significantly faster than any movement of the element being mapped. As such, the frequency shifts (Doppler shifts) in the echoes from blood are significantly larger than the Doppler shifts in the echoes from cardiac wall tissue. For example, for an ultrasound frequency of 5 MHz, the Doppler shift in echoes from blood is on the order of 5 kHz, whereas the Doppler shift in echoes from cardiac wall tissue is on the order of 1 KHz.

The processor analyzes the Doppler-shifted signals to find the positions and velocities of elements being imaged by the transducers. Because of the velocity difference between the liquid blood stream and the soft but solid tissue element, the Doppler shift due to the blood can be easily isolated (e.g., identified), to distinguish the surface of the element being mapped. The processor suppresses the blood Doppler-shifted component of the signal. For example, the processor may digitally filter out the Doppler-shifted components to completely remove them, or attenuates the blood-related spectral components by at least a given amount (e.g., by 20 dB). The resulting enhanced signals can then be used to reconstruct a blood-signal-free ultrasound image of the element.

In an embodiment, a processor receives echo signals reflected in response to ultrasound beam emitted from an array of ultrasound transducers in a catheter placed in a blood pool in an organ. The processor distinguishes, in the echo signals, between (i) first spectral signal components having Doppler shifts characteristic of blood and (ii) second spectral signal components having Doppler shifts characteristic of tissue of the organ. The processor suppresses the first spectral signal components relative to the second spectral signal components in the echo signals. Then, the processor reconstructs an ultrasound image of at least a portion of the organ from the echo signals having the suppressed first spectral signal components, and displays the reconstructed image to a user The phases of the 2D array of transducers can be electronically adjusted to focus at least a portion of the US wedge transmitted by the array on a target volume in the organ, such as a blood volume. This focusing effect may be used to temporarily increase the quality of the signals reflected from blood and/or from the cardiac wall, so as to enhance the Doppler measurement described above.

In some embodiments, the catheter also comprises an integral location sensor, such as a magnetic position sensor, that is pre-registered with the 2D array. Because of the integral location sensor, the spatial coordinates of every voxel in the imaged section are known. The processor can use the position measurements, for example, to overlay the blood-signal-free ultrasound image on another image (ultrasound or otherwise) of at least a portion of the heart.

Further to this, the processor can use the position measurements to register multiple ultrasound image sections, acquired by the 2D ultrasound transducer array, with one another. The processor then produces a union of the multiple registered ultrasound image sections, to form a rendering of at least a portion of the organ, and presents the rendering to a user.

In an embodiment, the processor performs the registration of the multiple ultrasound image sections while compensating for movements of the probe itself, or by compensating for movements due to respiration. In another embodiment, the processor produces the union by stitching the multiple ultrasound image sections one to another.

The processor can also adjust the phases of the driving signals to electronically steer the wedge, so that the imaged element (e.g., ostium of a pulmonary vein) is centered in a display showing the element.

System Description

FIG. 1 is a schematic, pictorial illustration of a catheter-based ultrasound imaging system 20 using a catheter 21 with a distal end assembly 40 comprising a 2D ultrasound-array 50 and a location sensor 52, in accordance with an embodiment of the present invention. Integral location sensor 52 is pre-registered with the 2D array 50 of catheter 21.

As seen, distal end assembly 40 is fitted at the distal end of a shaft 22 of the catheter. Catheter 21 is inserted through a sheath 23 into a heart 26 of a patient 28 lying on a surgical table 29. The proximal end of catheter 21 is connected to a control console 24. In the embodiment described herein, catheter 21 is used for ultrasound-based diagnostic purposes, although the catheter may be further used to perform a therapy such as electrical sensing and/or ablation of tissue in heart 26, using, for example, a tip electrode 56.

Physician 30 navigates distal end assembly 40 of catheter 21 to a target location in heart 26 by manipulating shaft 22 using a manipulator 32 near the proximal end of the catheter.

In an embodiment, 2D ultrasound-array 50, shown in detail in an inset 25, is configured to image a left atrium of heart 26. The recorded images are stored by processor 30 in a memory 37.

As seen in an inset 45, ultrasound array 50 comprises a 2D array 50 of multiple ultrasound transducers 53. Inset 45 shows ultrasound array 50 navigated to an ostium wall 54 of a pulmonary vein of the left atrium. In this embodiment, 2D array 50 is an array of 32×64 US transducers. The 2D array is able to image a section of the inner wall of the ostium.

Sensor 52 is configured to output signals indicative of a position, direction and orientation of the 2D ultrasound transducer array 52 inside the organ. A processor of the system is configured to register multiple ultrasound image sections, one with the other, using the signal output by the sensor acquired by the 2D ultrasound transducer array 50.

Because of the integral location sensor, the spatial coordinates of every pixel in the imaged section are known.

Control console 24 comprises a processor 39, typically a general-purpose computer, with suitable front end and interface circuits 38 for driving ultrasound transducers 53 (e.g., in a phased array manner that includes steering an ultrasound beam), and for receiving echo signals from transducers 53 for use by processor 39. Interface circuits 38 are further used for receiving signals from catheter 21, as well as for, optionally, applying treatment via catheter 21 in heart 26 and for controlling the other components of system 20. Console 24 also comprises a driver circuit 34 configured to drive magnetic field generators 36.

During the navigation of distal end 22 in heart 26, console 24 receives position and direction signals from location sensor 52 in response to magnetic fields from external field generators 36. Magnetic field generators 36 are placed at known positions external to patient 28, e.g., below table 29 upon which the patient is lying. These position and direction signals are indicative of the position and direction of 2D ultrasound-array 50 in a coordinate system of the position tracking system.

The method of position and direction sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

In some embodiments, processor 39 may be configured to operate array 52 in an electronic "sweeping mode" to image a large portion of a cardiac camber. In an embodiment, the imaged cardiac chamber (e.g., a left atrium) is presented to physician 30 by processor 39 on a monitor 27, e.g., in as a volume rendering 55.

Processor 39 is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise additional components and perform non-cardiac catheterizations.

Doppler Analysis in 3D to Image Heart Anatomy

Figure 2:
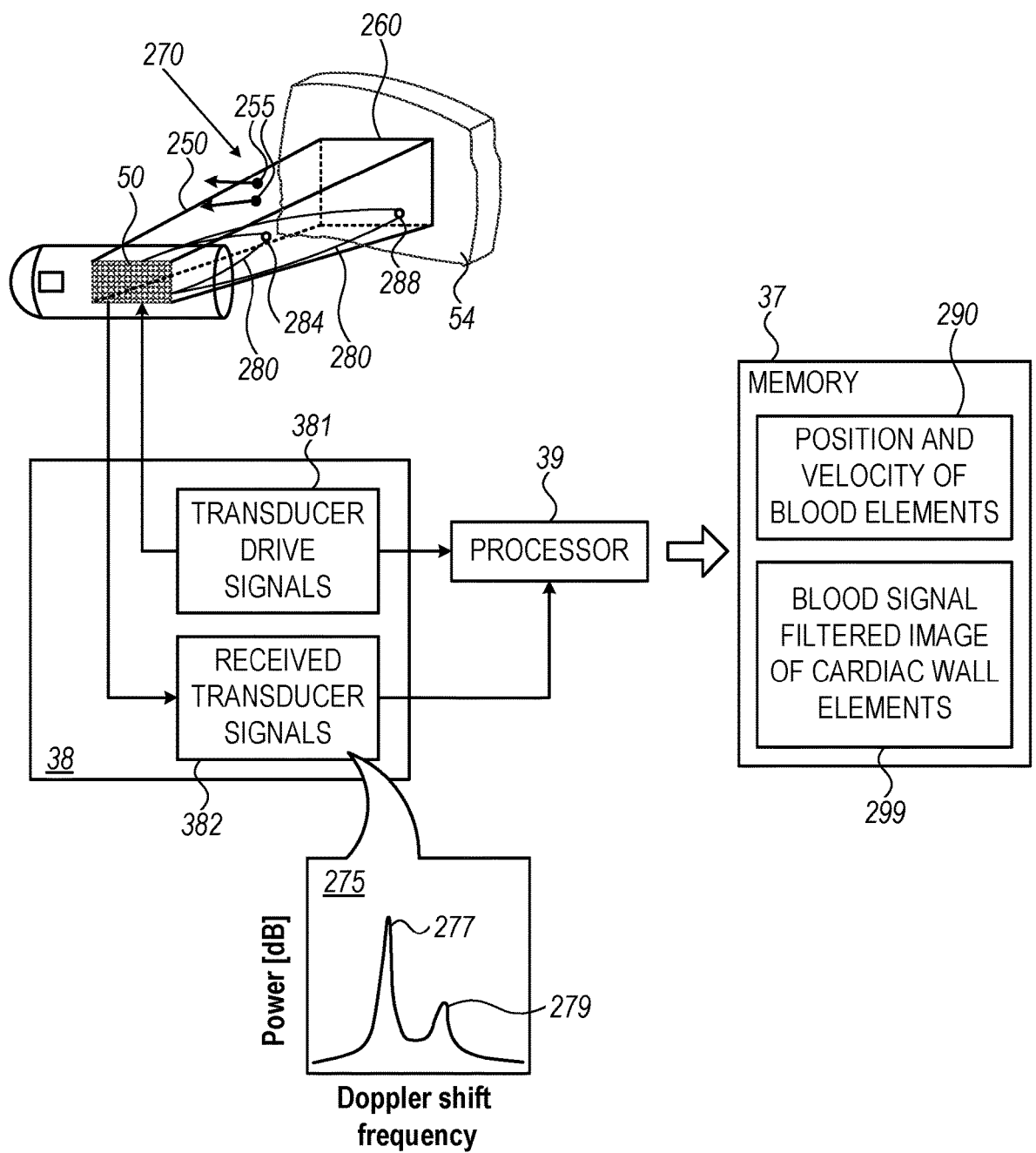
FIG. 2 is a schematic, pictorial illustration of a process for isolation of a blood Doppler-shifted component from an echo signal, followed by reconstruction of a blood-signal-free image by the system of FIG. 1, in accordance with an embodiment of the present invention.

FIG. 2 is a schematic, pictorial illustration of a process for isolation of a blood Doppler-shifted component from an echo signal, followed by reconstruction of a blood-signal-free image 299 by system 20 of FIG. 1, in accordance with an embodiment of the present invention.

The ultrasound signals are transmitted in a form of a wedge beam 250, and echoes are detected by the same phased array 50 of catheter 21.

As seen, the mode of acquisition of 3D wedge beam 250 enables simultaneous acquisition of a 2D image section 260 of a surface of an ostium wall 54 over which blood 255 travel in a blood stream with a velocity 270, e.g., out of a pulmonary vein.

Processor 39 provides driving signals via a transducer driving unit 381 of interface circuits 38 for the ultrasound transducers. A receiving unit 382 of interface circuits 38 receives the echo signals from the transducers.

A schematic graph 275 shows an example of a spectrum of a resulting echo signal from a certain wedge. As seen, a blood Doppler-shifted component 279 is well resolved from a tissue Doppler-shifted component 277. Therefore, processor 39 can isolate and remove or attenuate blood peak 279, or otherwise take blood peak 279 into account in a reconstruction model, so as to image the geometry of section 260 with high accuracy. In particular, this technique enables the processor to accurately image the boundary between the blood and the cardia wall tissue.

In an embodiment, processor 39 thus analyzes the received signals (e.g., received echoes) from the transducers via receiving unit 382 of interface circuits 38 to:
  (i) identify and filter out Doppler-shifted blood components from a signal, and, optionally, to derive position and velocity of blood elements 290; and
  (ii) generate an image 299 of soft tissue (e.g., of cardiac wall surfaces) using the blood-signal filtered signals (i.e., echo signals without blood Doppler-shifted components)

Processor 39 saves the above information in memory 37.

The processor may filter out or attenuate Doppler-shifted blood component 279 using digital filtration applied in various different ways to digital echo signals that were digitized by unit 382. For example, in one embodiment, the processor may apply frequency-domain filtering that removes signal components having Doppler shifts corresponding to blood velocity, and retains signal components having Doppler shifts corresponding to cardiac-wall velocity. In another embodiment, the processor defines, in the frequency domain, one range corresponding to blood velocity and another (lower-frequency) range corresponding to cardiac-wall velocity. The processor then suppresses the spectral range related to blood. Note that for this kind of filtering, the processor may use, for example, simple threshold comparison and may not need to identify any spectral peaks in the signal.

In yet another embodiment, the processor identifies only the blood component in order to remove it, without identifying the wall-tissue component. In a further embodiment, the processor identifies the slow wall-related spectral component, and suppress other signals.

As noted above, processor 39 may adjust the relative phases of the driving signals provided to the 2D array of transducers to focus at least a portion 280 of ultrasound wedge beam 250 transmitted by the array onto a blood volume 284. This focusing effect may be used to enhance the Doppler measurement described above. Additionally or alternatively, for example at a slightly different time, the processor may focus portion 280 on wall tissue surface area 288, to further enhance the Doppler imaging technique.

In an embodiment, to emit an ultrasound beam focused in a blood volume, the processor varies a focal length of the beam to collect a Doppler-shifted blood component from a location within this blood volume. By varying the locations, a blood velocity profile can be characterized by the processor, for example, over a path in blood between the catheter and the wall surface. The resulting blood velocity profile may be used in more elaborated (e.g., spatially weighted) removal of Doppler-shifted blood components of signals.

Figure 3:
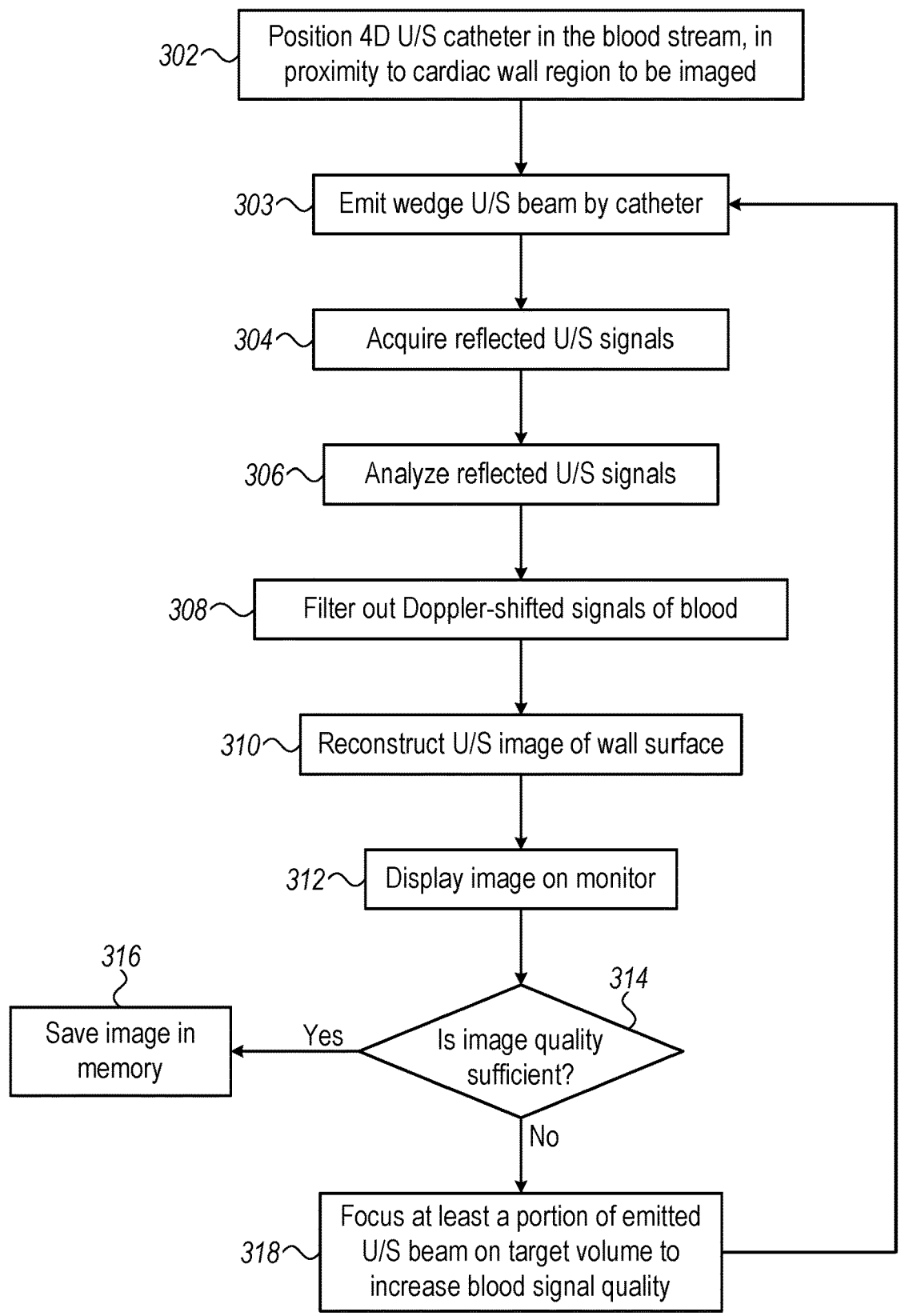
FIG. 3 is a flow chart that schematically illustrates a method of isolation of blood Doppler-shifted components from an echo signal to generate a filtered image using the system of FIG. 1, in accordance with an embodiment of the present invention.

FIG. 3 is a flow chart that schematically illustrates a method of isolation of blood Doppler-shifted components from an echo signal to generate a filtered image 299 using system 20 of FIG. 1, in accordance with an embodiment of the present invention.

The process begins in positioning 4D ultrasound (US) catheter 21 in the blood stream in proximity to cardiac wall tissue region to be imaged, such as near ostium wall tissue 54 of FIG. 1, at a catheter placement step 302.

Next, processor 39 commands the emission of wedge ultrasound (U/S) beam 250 by catheter 21, by applying driving signals to 2D-array 50, using unit 381, at US emission step 303.

In a return signal acquisition step 304, a reflected US signal is acquired by processor 39 using array 50 and unit 382.

Processor 39 analyzes reflected US signals to identify different Doppler-shifted components (e.g., components 277 and 279 of FIG. 2) of the echo signals, at signal analysis step 306.

Then, processor 39 filters out blood Doppler-shifted components from reflected signals, at blood signal filtration out step 308.

Using the blood-signal filtered out signals, processor 39 reconstructs a US image, such as image 299, of ostium wall tissue 54, at a wall surface image reconstruction step 310.

At a displaying step 312, processor 39 displays the reconstructed image on monitor 27.

A reviewer, such as physician 30, can decide (314) if the blood-signal filtered US image is of sufficient quality, and save the image in memory 37, at image saving step 316.

If physician 30 deems (314) that the quality of the image is not good enough, then, based on his/her input, processor 39 focuses a portion of the emitted US beam on blood volume, at US beam focusing step 318, to obtain an improved acquisition of blood signal, and the process returns to step 303.

The flow chart of FIG. 3 is brought purely by way of example for the sake of conceptual clarity. For example, using blood signals to obtain blood information 290 is omitted for simplicity. As another example, the processor may additionally electronically steer wedge 250 during acquisition.

Although the embodiments described herein mainly address cardiac applications, the methods and systems described herein can also be used in other body organs. For example, the disclosed technique can be used with visualizing large blood vessels of the body, such as located in the abdomen and the brain.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   emitting an ultrasound beam onto a blood volume from an array of ultrasound transducers in a catheter placed in a blood pool in an organ by providing driving signals to the array of ultrasound transducers, further comprising:
      adjusting relative phases of the driving signals provided to the array of ultrasound transducers to focus at least a portion of ultrasound beam onto a plurality of locations within the blood volume, the plurality of locations forming a path in blood between the catheter and a wall surface of the organ;
   characterizing a blood velocity profile over the path;
   receiving in the array echo signals reflected in response to the emitted ultrasound beam;
   distinguishing, in the echo signals, based on the blood velocity profile, between (i) first spectral signal components having Doppler shifts characteristic of blood and (ii) second spectral signal components having Doppler shifts characteristic of tissue of the organ;
   suppressing the first spectral signal components relative to the second spectral signal components in the echo signals;
   reconstructing an ultrasound image of at least a portion of the organ from the echo signals having the suppressed first spectral signal components; and
   displaying the reconstructed image to a user.

2. The method according to claim 1, wherein suppressing the first spectral signal components comprises filtering out the first spectral signal components from the echo signals.

3. The method according to claim 1, wherein suppressing the first spectral signal components comprises attenuating the first spectral signal components in the echo signals by at least a given amount.

4. The method according to claim 1, wherein the tissue of the organ is a wall tissue of a cardiac chamber.

5. The method according to claim 1, wherein focusing the emitted ultrasound beam comprises varying a focal length of the beam to variably collect blood Doppler shifted signals from different multiple blood volumes.

6. A system, comprising:
   a catheter comprising an array of ultrasound transducers, the array configured to be placed in a blood pool in an organ, to emit an ultrasound beam onto a blood volume and to receive echo signals reflected in response to the ultrasound beam; and
   a processor, which is configured to:
   provide driving signals to the array of ultrasound transducers;
   adjust relative phases of the driving signals provided to the array of ultrasound transducers to focus at least a portion of ultrasound beam onto a plurality of locations within the blood volume, the plurality of locations forming a path in blood between the catheter and a wall surface of the organ;
   characterizing a blood velocity profile over the path;
   distinguish, in the echo signals, based on the blood velocity profile, between (i) first spectral signal components having Doppler shifts characteristic of blood and (ii) second spectral signal components having Doppler shifts characteristic of tissue of the organ;
   suppress the first spectral signal components relative to the second spectral signal components in the echo signals;
   reconstruct an ultrasound image of at least a portion of the organ from the echo signals having the suppressed first spectral signal components; and
   display the reconstructed image to a user.

7. The system according to claim 6, wherein the processor is configured to suppress the first spectral signal components by filtering out the first spectral signal components from the echo signals.

8. The system according to claim 6, wherein the processor is configured to suppress the first spectral signal components by attenuating the first spectral signal components in the echo signals by at least a given amount.

9. The system according to claim 6, wherein the tissue of the organ is a wall tissue of a cardiac chamber.

10. The system according to claim 6, wherein the array is configured to focus the emitted ultrasound beam by varying a focal length of the beam to variably collect blood Doppler shifted signals from different multiple blood volumes.

\* \* \* \* \*